United States Patent [19]

Lützke

[11] Patent Number: 4,474,070

[45] Date of Patent: Oct. 2, 1984

[54] METHOD AND APPARATUS FOR MEASURING PARTICULATES IN A WASTE GAS

[75] Inventor: Klaus Lützke, Duisburg, Fed. Rep. of Germany

[73] Assignee: Rheinisch-Westfälischer Technischer Überwachungsverein e.V., Essen, Fed. Rep. of Germany

[21] Appl. No.: 417,372

[22] Filed: Sep. 13, 1982

[30] Foreign Application Priority Data

Sep. 16, 1981 [DE] Fed. Rep. of Germany ....... 3136646

[51] Int. Cl.³ ............................................. G01N 31/00
[52] U.S. Cl. ....................................... 73/863.12; 73/28
[58] Field of Search ........... 73/863.21, 863.12, 863.11, 73/28

[56] References Cited

U.S. PATENT DOCUMENTS

| | | | |
|---|---|---|---|
| 3,517,557 | 6/1970 | Granger et al. | 73/863.12 |
| 3,892,549 | 7/1975 | Lyshkow | 73/863.12 |
| 4,034,611 | 7/1977 | Horling | 73/863.12 |
| 4,154,088 | 5/1979 | Werner | 73/863.12 X |
| 4,324,146 | 4/1982 | Born | 73/863.21 X |
| 4,324,234 | 8/1982 | Bernath | 73/863.12 |

Primary Examiner—Gerald Goldberg
Assistant Examiner—Vincent P. Kovalick
Attorney, Agent, or Firm—Karl F. Ross; Herbert Dubno

[57] ABSTRACT

A method of and an apparatus for measuring the solids content of a hot waste gas wherein the hot waste gas, without cooling, is mixed with a cool gas so that the mixture is at a reduced temperature at which substances in the sample are transformed into the solid state and the sample is cooled without condensation. The gas mixture is then passed through a measuring filter on which the solids are collected. The mixture is preferably formed coaxially.

10 Claims, 1 Drawing Figure

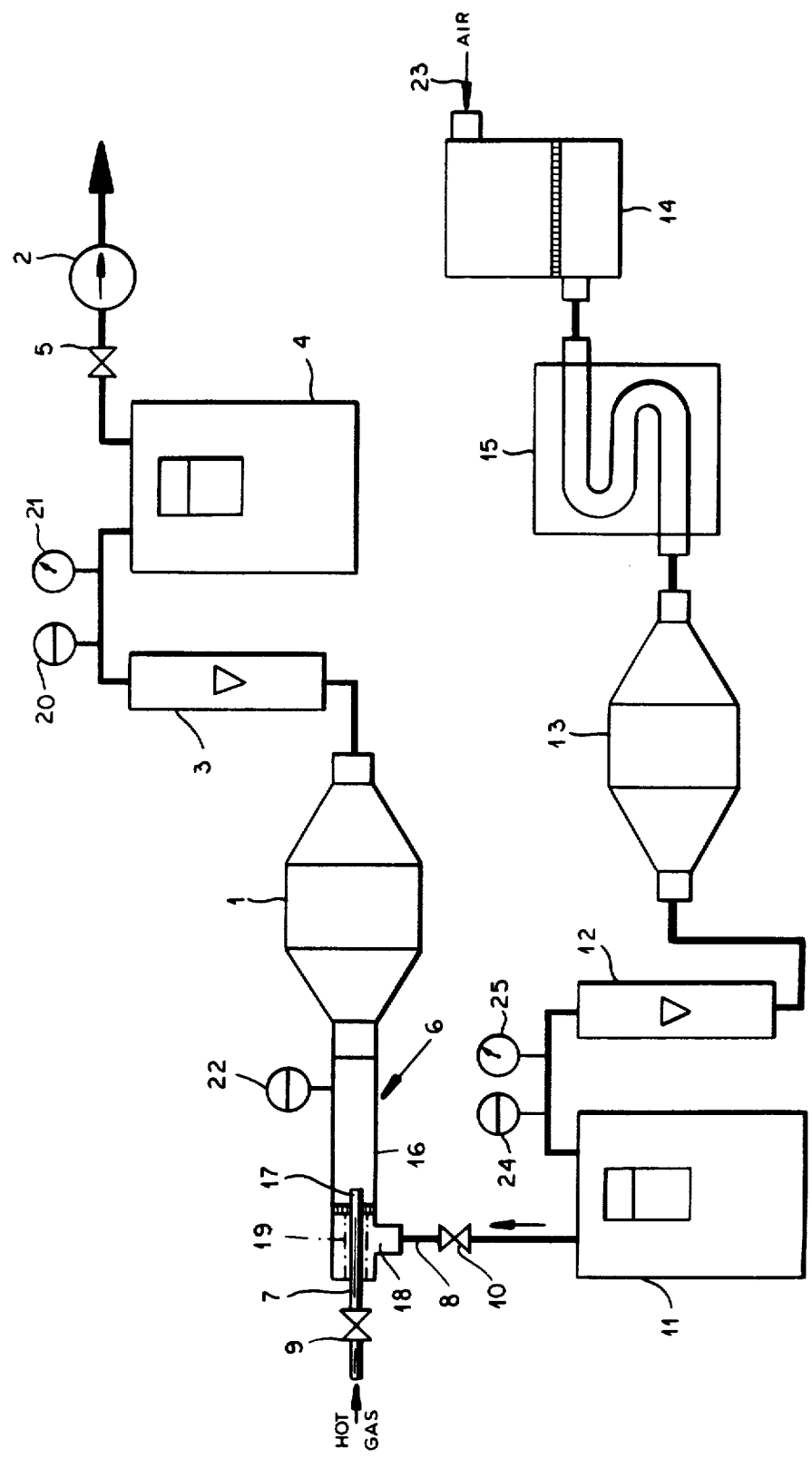

METHOD AND APPARATUS FOR MEASURING PARTICULATES IN A WASTE GAS

FIELD OF THE INVENTION

My present invention relates to a method of and to an apparatus for measuring the solids content or concentration of a waste gas and, more particularly, to a system for determining the particulate solids content of hot furnace and like exhaust gas.

BACKGROUND OF THE INVENTION

It is frequently desirable, for process control purposes, for regulating the efficiency of a plant or a unit of a plant, for compliance with environmental protection regulations, and for a variety of other reasons, to measure the solids content or concentration of a hot waste gas, e.g. a gas generated by a furnace, or in a chemical or metallurgical plant or elsewhere.

The term "waste gas" is used herein in its broadest sense to refer to any hot exhaust, waste or product gas which may be further processed or simply discharged, no matter how derived. Typical of an exhaust gas with which the present invention is concerned is the gas derived from a thermal power plant boiler, generally prior to gas cleaning and, of course, prior to discharge of the gas into the atmosphere. However, the invention is generally applicable to any system in which determination of the solids content of a hot gas is desirable.

In practice, the measurement of the solids content of a hot waste gas has been effected in the past by diverting a sample of this hot waste gas through a measuring line which includes a measuring filter upon which the solids collect and from which the solids content can be determined, a flowmeter indicating the rate of flow of the sample, and a gas meter signaling the volume of the gas which has been processed.

While this system is effective to provide some indication of the solids content of the waste gas, a problem is encountered when the waste gas temperature is relatively high, since at extremely high temperatures, some of the components which are normally considered to be solids may be in a gaseous or liquid state. Furthermore, simply allowing the sample to cool does not always provide a true indication of solids content because of the different states of aggregation of particles within the gas and the nonuniformity of changes of state which can occur.

The problem is pronounced where the gases contain polycyclic aromatics which tend to accumulate upon the dust particles and undergo changes in composition or state and various transformations at high temperatures.

Thus, earlier systems for determing the solids content of high temperature waste gases were inaccurate when the measurement was effected at high temperature and created additional problems when attempts were made simply to cool the gas sample before measurement.

OBJECTS OF THE INVENTION

It is the principal object of the present invention to provide a method of measuring the solids content of a hot exhaust gas whereby the aforementioned disadvantages are avoided and a measurement can be made in a simple and effective manner which is accurate and reproducible.

Another object of this invention is to provide an improved apparatus for measuring the solids content of a hot exhaust gas.

SUMMARY OF THE INVENTION

These objects and others which will become apparent hereinafter are attained in accordance with the invention which is based upon my surprising discovery that the aforedescribed disadvantages can be avoided by continuously diluting the hot exhaust gas simply by mixing it before it enters the filter with a particle-free cool gas so that as a result of this dilution a complete solids phase is formed at the lower mixture temperature to which the hot exhaust gas is cooled in aa condensation-free manner, the waste gas being then drawn through the measuring filter, the flow-velocity measuring device and the gas meter.

According to the invention, therefore, a sample of the hot exhaust gas, before it encounters the measuring filter, is mixed with a quantity of a cool gas which has previously been freed from all solids so that this dilution or cooling gas does not contribute any solids to the mixture and, the mixture is thereby brought to a solid-phase forming reduced mixing temperature without the formation of condensate.

The invention is based upon my discovery that this approach to cooling of the hot sample can reduce the temperature without permitting the condensation process to interfere and yet can transform all of the materials which are solid at the reduced temperature into the solid state (hence reference to the solid phase) even if such substances were in a gaseous or liquid state in the hot sample.

Apparently this is the result of the simultaneous cooling and dilution .

The reduced mixture temperature of the invention is of course any temperature less than the temperature of the hot exhaust gas at which accurate measurement of the solids content can be effected, this temperature being preferably sufficiently low that all of the substance entrained in the gas and which constitutes the particles, is exclusively in the solid phase. This means that, in the case of polycyclic aromatics, for example, where originally some of this substance may be in a solid phase while some may be in a vapor or liquid phase, e.g. as a coating on dust particles, at the reduced temperature, all are in the solid phase.

Since the collection of the particles takes place at a reduced temperature as well, decomposition of such materials on the filter is avoided.

The cooling gas can be ambient air, nitrogen, or the like and is preferably subjected to drying, cooling and prefiltration before it is metered into the gas sample.

The prefiltration precludes the addition of solids to the sample which may introduce discrepancies in the results.

In a preferred mode of carrying out the invention, the sample gas stream and the cooling gas stream are fed in parallel as partial gas streams and are then combined, with the cooling gas stream being conveyed coaxially to the sample gas stream therearound. In this way, the cooling gas stream forms a shield between the sample gas stream and the walls of the mixing passage, at least initially, to prevent the particles from depositing on these walls.

I have found, further, that condensation can be avoided by thermally insulating the sample gas stream or even heating the latter to maintain its temperature until mixing occurs.

In most cases, the desired reduced temperature of less than 40° C. can be obtained with a volume ratio of the cooling gas to the sample gas of 10:1. Of course other ratios are possible under the conditions described.

In its apparatus aspects, the present invention provides a device which comprises in addition to the measuring filter, a suction means for drawing the sample through the filter, and a flow-velocity meter and a gas meter (volumetric measuring unit), interposed between the filter and the suction means.

According to the invention, moreover, a mixing device is provided with a sample gas inlet, a cooling gas inlet, control means for the gases and means for measuring the cooling gas flow, for drying it, for filtering it, etc.

Especially when ambient air is used as the cooling gas, drying means is required.

When the gas meter is provided, it preferably is of the bellows type. The suction means can be any conventional pump or ejector arrangement and the control means can be provided to adjust the sample gas volume, the cooling gas volume and the volume of the mixture. It has been found that the system of the invention can be used very effectively for measuring particles in flowing gases in accordance with the VDI standard 2066.

The volume of the sample can be determined from the difference of the values obtained from both gas meters.

Preferably the mixing device is a mixing tube into which a pipe carrying the gas sample extends, this pipe being surrounded by a heater or insulating layer and the cooling gas fitting opening into the mixing tube around the sample pipe.

A key advantage of the present invention is that the measuring process does not act upon a phase mixture of gaseous, liquid and solid particles and hence is greatly simplified. The system is effective even for materials with high vapor pressure, such as mercury and arsenic and has been found to be effective not only for power plant and engine waste gases, but also for the waste gases of coking and glass-making furnaces or pots.

BRIEF DESCRIPTION OF THE DRAWING

The above and other objects, features and advantages of the present invention will become readily apparent from the following description, reference being made to the accompanying drawing in which the sole FIGURE is a flow diagram illustrating the apparatus for carrying out the present invention.

SPECIFIC DESCRIPTION

The apparatus shown in the drawing comprises a measuring filter 1 of any conventional design and position in which particulates can be collected for analysis, e.g. by weighing.

The measuring filter 1 is provided in line with a suction means, e.g. a suction pump 2 and between a filter 1 and the suction pump 2, there is provided a flowmeter 3 displaying the flow velocity, and a gas meter 4, preferably a bellows gas meter, capable of measuring the flow volume. A pressure accumulator 20 and a gauge 21 are also provided to prevent pressure surges, on the one hand, and to indicate the suction pressure developed by the pump 2 downstream of the filter 1. The flow rate is controlled by a valve 5 between pump 2 and the gas meter 4.

According to the invention, upstream of the measuring filter 1, there is provided a mixing device 6 having a sample gas inlet 7, a cooling gas inlet 8 and a pressure accumulator 22 which levels pressure surges upstream of the filter 1.

The inlets 7 and 8 are provided with respective control devices 9 and 10, i.e. respective valves which can adjust the relative rates of flow of the sample gas and the cooling gas.

In the embodiment illustrated, the cooling gas is ambient air. The ambient air at 23 is drawn into a dryer 14 of any conventional design, e.g. a bed of anhydrous calcium chloride, the dry air flowing through a cooler 15 and a particular filtering device 13 to insure complete removal or particles from the cooling air.

The cooling air then flows through the flowmeter 12 and the bellows-type gas meter 11 to the inlet 8. A pressure accumulator 24 and a pressure gauge 25 are provided for the cooling air as well.

The mixer 6 is provided with a mixing tube 16 into which the sample gas is admitted via coaxial tube 17 surrounded by a heating element 19 to prevent premature cooling of the sample gas without dilution. Around the tube 17, in an annular compartment 18, the cooling gas is introduced so that it flows axially into the tube 16 around the sample gas as it mixes therewith.

The temperature of the mixture is thus brought to a level well below the sample gas temperature without the formation of condensate. The solids are collected at 1 and the sample gas volume determined by the difference between the readings at units 4 and 11 so that the solids concentration can be readily determined.

I claim:

1. A method of determining the solids contents of a hot waste gas which comprises the steps of:
   (a) displacing along a predetermined path a sample of the hot waste gas containing at least some substances which are solid at a lower temperature than that of the waste gas but are as the same substances in a fluid phase at the temperature of said waste gas;
   (b) diluting and cooling said sample by continuously mixing therewith a cool gas at a temperature below said lower temperature to form a mixture at said lower temperature and thereby transform said substances from the fluid phase into a solid phase without the formation of a condensate in said mixture; and
   (c) drawing said mixture through a measuring filter in which solids are collected from said mixture and through a flowmeter and a gas volume meter.

2. The method defined in claim 1 wherein said cool gas is ambient air, further comprising the step of drying said ambient air and filtering said ambient air before mixing same with said sample.

3. The method defined in claim 1 wherein said sample and said cool gas are mixed by introducing them together into a mixing tube with said cool gas being introduced into said tube around said sample for directly mixing therewith.

4. The method defined in claim 1, further comprising the step of maintaining said sample at temperature above said lower temperature until it mixes with said cool gas.

5. The method defined in claim 1 wherein said lower temperature is less than 40° C. and said cool gas is mixed with said sample in a volume ratio of substantially 10:1.

6. An apparatus for measuring the solids content of a hot waste gas, comprising:

a measuring filter capable of collecting solids from a gas mixture drawn therethrough;

suction means connected to said measuring filter for drawing said mixture therethrough;

means for measuring the gas flow between said filter and said suction means;

a mixing chamber upstream of said filter receiving a sample of a hot waste gas; and means for supplying a cool gas to said mixing chamber and including a prefilter for filtering said cool gas, a dryer for drying said cool gas, a flowmeter for measuring the velocity of said cool gas and a gas meter for measuring the volume of said cool gas connected in series.

7. The apparatus defined in claim 6 wherein said mixing chamber is a mixing tube provided with a pipe for coaxially admitting said sample thereto, said cool gas being admitted to said tube around said pipe and directly into admixture therewith.

8. An apparatus defined in claim 7, further comprising means for maintaining the temperature of said sample at a level above that at which a condensate can form therein unitl it mixes with said cool gas.

9. The apparatus defined in claim 8 wherein the last mentioned means includes heating means around said pipe.

10. The apparatus defined in claim 8 wherein the last mentioned means includes insulation surrounding said pipe.

* * * * *